United States Patent
Webler, Jr.

(10) Patent No.: US 8,172,831 B2
(45) Date of Patent: May 8, 2012

(54) CATHETER CONFIGURED FOR INCREMENTAL ROTATION

(75) Inventor: William E. Webler, Jr., San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/328,518

(22) Filed: Dec. 4, 2008

(65) Prior Publication Data

US 2010/0057050 A1  Mar. 4, 2010

Related U.S. Application Data

(60) Provisional application No. 61/093,701, filed on Sep. 2, 2008.

(51) Int. Cl.
*A61M 25/00* (2006.01)

(52) U.S. Cl. .................................. 604/525; 604/523

(58) Field of Classification Search .............. 604/525, 604/528, 532, 523
See application file for complete search history.

(56) References Cited

U.S. PATENT DOCUMENTS

| | | | |
|---|---|---|---|
| 5,741,429 A | | 4/1998 | Donadio et al. |
| 6,352,531 B1 * | | 3/2002 | O'Connor et al. ............. 606/15 |
| 6,855,124 B1 * | | 2/2005 | Gonzalez et al. .......... 604/96.01 |
| 2004/0243102 A1 * | | 12/2004 | Berg et al. .................... 604/525 |
| 2005/0124977 A1 * | | 6/2005 | Gonzalez et al. ............ 604/534 |
| 2007/0129792 A1 | | 6/2007 | Picart et al. |

FOREIGN PATENT DOCUMENTS

| | | |
|---|---|---|
| DE | 41 04 092 | 8/1991 |
| WO | WO 2006/122147 | 11/2006 |
| WO | WO 2007/108775 | 9/2007 |

OTHER PUBLICATIONS

Invitation to Pay Additional Fees for PCT/US2009/055787, mailed Jan. 12, 2010, 5 pgs.
International Search Report for PCT/US2009/055784, mailed Mar. 29, 2010, 12 pgs.
Veerabadran et al. "Nanoencapsulation of Stem Cells within Polyelectrolyte Multilayer Shells" Macromolecular Bioscience, vol. 7, pp. 877-882 (2007).
Yim et al., "Proliferation and differentiation of human mesenchyma stem cell encapsulated in polyelectrolyte complexation fibrous scaffold", Biomaterials, vol. 27, pp. 6111-6122 (2006).

* cited by examiner

*Primary Examiner* — Kevin C Sirmons
*Assistant Examiner* — Brandy C Scott
(74) *Attorney, Agent, or Firm* — Squire Sanders (US) LLP (57) ABSTRACT

A catheter which allows the rotational orientation of the distal end of the catheter to be adjusted in discrete intervals as the physician rotates the proximal end of the catheter. The catheter is designed to intentionally induce whipping but to limit the amount of whipping to a desired rotational interval.

22 Claims, 2 Drawing Sheets

CATHETER CONFIGURED FOR INCREMENTAL ROTATION

BACKGROUND OF THE INVENTION

The invention relates to the field of medical devices, and more particularly to catheters, such as needle catheters or other elongated devices configured for inserting into a patient's body lumen or cavity to perform a diagnostic and/or therapeutic procedure.

During a treatment or diagnostic procedure using an interventional catheter slidably disposed in a patient's coronary or peripheral vasculature, it may be necessary to rotate the catheter to properly position an operative distal end component in a specific rotational orientation relative to the treatment location in the patient's anatomy. For example, in a drug delivery procedure using a needle catheter, the ability to rotate the distal tip of the catheter would facilitate performing injections at multiple adjacent locations to more fully treat an area of the patient's anatomy. Typically, the physician attempts to orient the distal end of the catheter inside the patient by rotating the proximal end of the catheter outside the patient. However, in the construction of elongated intravascular catheters, one difficultly has been the tendency of the catheter shaft to exhibit wind-up and whipping in the anatomy, which makes it difficult to accurately orient the operative distal end at equally spaced rotational intervals by rotating the proximal end of the catheter.

As the physician rotates the proximal end of the catheter during a procedure, at the start of rotation, friction on the device outer diameter and energy loss due to dampening (and overcoming any curve preset in the shaft) requires that a torque and an amount of rotation be applied to the proximal end of the shaft before the distal portion begins to rotate. In other words, some amount of energy is stored in the shaft and some amount of energy is converted to heat prior to its distal portion beginning to rotate. This rotation required to overcome friction and damping is called wind-up. During rotation, as the amount of stored energy in the shaft increases, this extra required energy is obtained by reducing the amount of the rotation of the distal end of the shaft relative to the proximal end, causing an increased proximal applied torque. Conversely, during rotation, as the amount of stored energy in the shaft decreases, this released energy causes the amount of the rotation of the distal end of the shaft relative to the proximal end to increase, causing a decreased proximal applied torque. When the proximal end of the shaft is rotated at a constant rate, the distal end of the shaft will tend to remain at or near (rotate slowly at) rotational orientations with minimum stored energy, rotate rapidly when approaching the rotational orientations where the shaft stores a minimum amount of energy relative to adjacent orientations, rotate slowly when approaching the rotational orientations where the shaft stores a maximum amount of energy relative to adjacent orientations, and to rapidly rotate or jump past the orientations with a maximum energy storage. This is called whipping.

The physical basis of whipping is the variation with rotational orientation of the flexural modulus or bending moment of the catheter shaft when it is confined in a curved conduit such as the patient's aortic arch or other curved anatomy, or a curved section of a guide catheter. This causes the amount of stored energy in the shaft to vary with rotational angle in a shaft portion that is rotated while it is confined in the curved conduit, thus producing the maximum and minimum energy storage rotational orientations that result in the whipping. Because unintentionally induced whipping can make it very difficult or impossible to adequately control the distal rotational orientation of the device by rotating the proximal end, a design objective in many conventional percutanteous catheters, especially where rotational orientation control is desired, is to minimize whipping. A variety of features and conditions are considered in the design of catheter shafts to minimize whipping. In general, all other factors being equal, the least whipping and wind-up occurs in shafts with the highest torsion modulus to flexural modulus ratio. Additionally, designing and processing a shaft (i.e., the entire length of the shaft or just a section thereof) to have a consistent flexural modulus/bending moment as it is rotated regardless of the rotational orientation of a bend applied to the shaft, and avoiding setting a bend in the shaft, will minimize whipping. However, a consistent flexural modulus may require features such as consistent wall thickness, consistent/linear elastic material properties, the spiraling of shaft components, and/or concentric shaft designs, which are most often not practical to include or obtain.

With catheters having a pre-set bend formed in the shaft, the bending moment and energy storage of the catheter shaft is minimized when the pre-set bend of the catheter shaft portion aligns with a curve of a conduit such as the patient's vasculature or guiding catheter, and the catheter preferentially assumes this rotational orientation. However, this results in the catheter being limited to a single easily attained rotational orientation relative to the curved conduit, and is not useful when two or more catheter rotational orientations relative to the curved conduit, or a rotational increment of other than 360 degrees, are desired.

It would be a significant advance to provide catheters that allow for accurate control of the distal rotational orientation of the device by rotating the proximal end.

SUMMARY OF THE INVENTION

This invention is directed to a catheter which allows the rotational orientation of the distal end of the catheter to be adjusted in discrete intervals as the physician rotates the proximal end of the catheter. The catheter is designed to intentionally induce whipping in a controlled manner in which the rotational spacing of the shaft minimum energy storage rotational orientations is set to the desired rotational interval, and/or an operative distal end portion of the catheter is in a desired rotational orientation relative to a shaft minimum energy storage rotational orientation. As a result, the operative distal end of the catheter is easily and accurately oriented in a patient's body lumen during a medical procedure, which can result in a number of benefits such as more accurately and thoroughly treating or diagnosing a region in a shorter amount of time.

A catheter of the invention generally has an elongated shaft with a section of the shaft having incremental rotation inducing features configured to induce incremental whipping when the shaft section is confined in a curved conduit, which may be an anatomical curved conduit such as the curve of the patient's aortic arch, or a curved conduit of a guiding catheter used to position the catheter of the invention. The incremental rotation inducing features are positioned on the catheter closer to an operative distal end portion of the catheter than to the proximal portion of the catheter where the rotation of catheter is controlled. The incremental rotation inducing features comprise one or more longitudinal shaft portions of higher or lower flexural modulus than circumferentially surrounding longitudinal shaft portions, and more typically comprise two or more longitudinal shaft portions of a lower flexural modulus circumferentially spaced apart around the shaft section, with longitudinal shaft portions therebetween of a higher flexural modulus. In general, when the longitudinal shaft portions of a lower flexural modulus are rotated in a confining curved conduit such that it is oriented toward the inside of the bend of the curved conduit, the shaft stored energy is at a minimum. Conversely, when the longitudinal shaft portions of a high flexural modulus are oriented toward the inside of the bend of the curved conduit, the shaft stored energy is at a maximum. As a result, as the section of the catheter is arcing through the bend of the curved conduit, any given rotational orientation the shaft will be an orientation that stores either more or less energy relative to an adjacent rotational orientation. The incremental rotation inducing features of the catheter shaft will thus rotate rapidly through the maximum shaft stored energy rotational orientations and slow/stop rotating as the shaft is at or near a rotational orientation with minimum shaft stored energy, and the circumferential spacing between the lower flexural modulus strips of the catheter of the invention will define the increment (i.e., degrees of rotation) that the shaft section rotates in response to rotation at the proximal end of the catheter shaft.

A method of the invention, which orients an operative distal portion of a catheter in a patient's body lumen for performing a medical procedure, generally comprises advancing a catheter of the invention within a patient's body lumen to position the operative distal portion of the catheter at a desired region in the patient's anatomy, and inducing controlled whipping in rotational increments to orient the operative distal portion of the catheter at a desired rotational orientation in the patient. More specifically, the catheter shaft comprises a tubular member having an incremental rotation inducing section along which a wall of the shaft has two or more strips circumferentially spaced apart by portions of the wall having a different flexural modulus than the strips, such that longitudinal shaft portions of are separated circumferentially by longitudinal shaft portions of a lower flexural modulus configured to provide the shaft in a curved configuration with two or more relatively low stored energy rotational orientations separated by two or more higher stored energy rotational orientations. The incremental rotation is induced by positioning the incremental rotation inducing section of the shaft in a curved section of a delivery catheter and/or in a curved section of the patient's body lumen, and then rotating the proximal end of the shaft by an amount which thereby places the shaft section under torsion force (torque) which rotates the incremental rotation inducing section of the shaft and thus rotates the distal end of the shaft in a rotational increment resulting from the circumferential spacing between the strips (of the incremental rotation inducing section) as the shaft twists through one of the maximum stored energy orientations to one of the minimum stored energy orientations, one or more times. During catheter rotation, the operator or the machine performing the rotation may detect the increase in required applied torque as a maximum energy storage orientation is approached and the subsequent decrease in the required applied torque as the maximum storage orientation is passed and the shaft section rotates to or near to the next minimum storage orientation A variety of suitable configurations can be used to form the incremental rotation inducing section of the shaft. Preferably, the rotation inducing section is readily manufacturable, and is configured such that the rotation inducing features do not disadvantageously affect other catheter performance issues such as torquability, kink resistance, pushability, fluid transport and trackability. The rotation inducing section is also preferably not traumatic to the patient anatomy, for example by not including or covering pinch points, sharp edges or rough surfaces that can damage tissue. A variety of elongated intracorporeal devices can be configured according to the invention, and generally have a tubular shaft and an operative distal end that requires rotational orientation control. In one presently preferred embodiment, the catheter is a needle catheter having a needle port in a distal shaft section. However, a catheter of the invention could have any number of operative distal end components requiring rotational orientation control including a port, a sensor, and the like. Therefore, the term "catheter" as used herein should be understood broadly to refer to a variety of elongated intravascular or other intracorporeal devices.

Generally, a catheter of the invention has two or more strips of either higher or flexural modulus material in or on a wall of the catheter shaft. Higher flexural modulus strips consist of a higher modulus wall material or structure and lower flexural modulus strips consist of a lower modulus wall material and/or structure, which replace and/or add to the wall material proximal and/or distal to the strips and the strips are circumferentially spaced apart by continuous portions of the wall, and the strips are longitudinally extending along a portion of catheter forced to assume the curved shape during the medical procedure.

In a presently preferred embodiment, a catheter configured for controlled whipping in rotational increments, which assumes a curved shape in a patient's vasculature to position an operative distal portion for performing a medical procedure, generally comprises an elongated tubular shaft having a proximal end, a distal end, a lumen therein, and two or more strips of voids in a wall of the shaft. The voids preferably consist of the space left by eliminating wall material, and the strips are circumferentially spaced apart by continuous portions of the wall, and extend substantially longitudinally along a portion of catheter forced to assume the curved shape during the medical procedure. The strips of voids produce lower flexural modulus longitudinal portions of the shaft wall.

In another embodiment, a catheter of the invention generally comprises an elongated tubular shaft having a proximal end, a distal end, and a tubular member with a section along which a wall of the shaft has two or more strips circumferentially spaced apart by portions of the wall having a different flexural modulus than the strips, and along which the shaft has an average flexural modulus (averaged over a full rotation) substantially equal to an average flexural modulus of longitudinally adjacent portions of the shaft along which the strips do not extend. The different flexural modulus strips (i.e., the flexural modulus along the strips is increased or decreased relative to the portions of the shaft wall circumferentially spaced between the strips) could be formed by the voids of the previous embodiment or by a variety of suitable methods including strips of higher or lower modulus material in or on the shaft. However, despite the presence of the different flexural modulus strips, an average flexural modulus of the shaft does not change relative to immediately adjacent proximal and distal sections of the shaft which don't have the strips. As a result, larger differences in energy storage between the maximum and minimum shaft energy storage rotational orientations may be attained while minimizing kinking, torsion buckling or other failures of the shaft at the incremental rotation inducing section. Larger differences in energy storage between the maximum and minimum shaft energy storage conditions may be desired to make the applied torque changes during catheter rotation more detectable and/or to increase rotational increment precision. Failures of the shaft which would otherwise be made more likely (i.e., caused to occur at lower force levels) by the presence of the incremental rotation inducing section can additionally or alternatively be prevented or minimized (i.e., caused to occur at higher force levels) by limiting the difference between the stored energy of the maximum and minimum stored energy orientations (i.e., the flexural modulus provided by the different flexural strips is not disadvantageously much greater or lesser than the flexural modulus of the shaft wall portions circumferentially therebetween).

A catheter of the invention has a distal end that rotates a desired increment in response to rotation of the proximal end of the catheter. Moreover, in preferred embodiments, the catheter provides the user with tactile feedback of the incremental rotation. Thus, a flexible shaft of sufficient length can be rotated at one end to effect an incremental rotation at its other end, a portion of which other end is confined in a curved conduit, in a manner that can be detected or otherwise controlled by the physician. These and other advantages of the invention will become more apparent from the following detailed description and accompanying exemplary drawings.

DETAILED DESCRIPTION OF THE PREFERRED EMBODIMENTS

Figure 1:
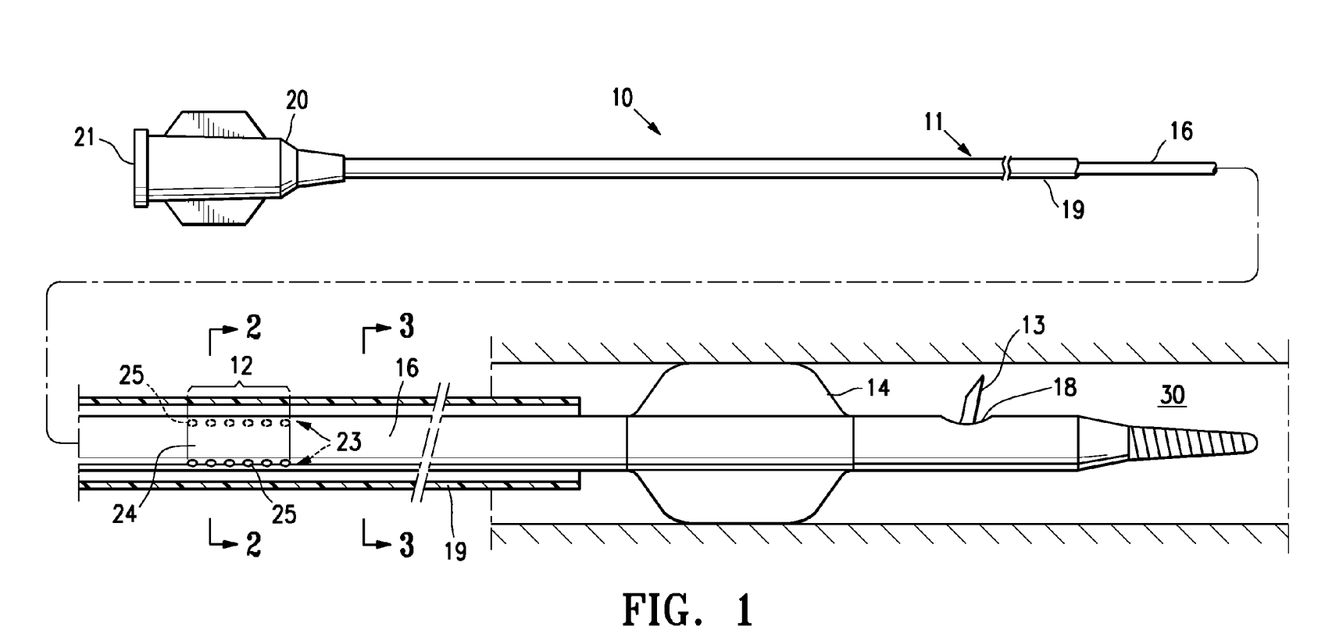
FIG. 1 is an elevational, partially in section, view of a needle catheter embodying features of the invention having incremental rotation inducing features.

FIG. 1 is an elevational, partially in section, view of a catheter 10 embodying features of the invention, generally comprising an elongated tubular shaft 11 having a proximal end, a distal end, and incremental rotation inducing features 12 in a wall of the shaft 11. The catheter 10 is a needle catheter having a needle 13 which is slidably disposed in the shaft 11 and which reversibly extends from the shaft in an extended configuration. In the illustrated embodiment, the needle catheter 10 further includes a radially expandable member 14 mounted on a distal shaft section. The radially expandable member 14 is configured to expand against the inner surface of the patient's body lumen 30, to thereby temporarily center and stabilize the location of the catheter in the body lumen 30. A variety of suitable radially expandable members 14 can be used including open-walled cages or inflatable balloons. In an embodiment in which the expandable member 14 is a balloon with an inflatable interior, an inflation lumen is provided in the elongated shaft 11 in fluid communication with an inflation fluid source at a proximal adapter port for inflating/deflating the balloon, and the deployment sheath 19 would typically be omitted.

In the embodiment of FIG. 1, the shaft 11 comprises an inner member 16 (i.e., "needle sheath") with a flexible tip and a lumen 17 (see FIGS. 2 and 3) which extends to a port 18 and which has the needle 13 slidably disposed therein, and an outer deployment sheath member 19 slidably disposed on the inner member 16. In the illustrated embodiment, the expandable member 14 is an open-walled cage typically configured to radially self-expand to the expanded configuration illustrated in FIG. 1 from a collapsed configuration (not shown) upon removal of a radially restraining force, such as when the deployment sheath 19 is proximally retracted from an advanced configuration surrounding the cage 14 to the retracted configuration illustrated in FIG. 1. A proximal handle/adapter 20 on a proximal end of the shaft 11 controls extension and retraction of the needle 13 and of the sheath member 19, and has a port 21 configured for connecting to a fluid source (not shown) for infusion within a lumen 15 of the hollow needle 13 during an agent delivery procedure. In the illustrated embodiment, the needle 13 extends transversely from the shaft at a location proximal to the distal end of the device. The rotational orientation of port 18 relative to the body lumen 30 prior to needle 13 extension controls the location at which the needle 13 pierces the wall of the body lumen 30.

The incremental rotation inducing features 12 in the embodiment of FIG. 1 generally comprise a shaft section having two strips 23 circumferentially spaced apart by portions 24 of the wall having a different flexural modulus than the strips 23. In the illustrated embodiment, the incremental rotation inducing features 12 are in a wall of the inner member 16 of the shaft 11, and the strips 23 comprise voids 25 in the wall of the inner member 16, circumferentially spaced apart by continuous portions 24 of the wall. The composition of the wall of the shaft section is otherwise the same around the circumference of the shaft. Thus, longitudinal shaft portions 23 are separated circumferentially by longitudinal solid walled portions 24 of a higher flexural modulus, configured to provide the shaft in a curved configuration with two or more relatively low stored energy orientations separated by higher stored energy orientations. Each strip 23, formed by voids 25, is substantially axially extending (i.e., longitudinally straight within normal manufacturing tolerances without a substantial circumferential twist intentionally provided in the path of the voids). In the embodiment of FIG. 1, each strip 23 is formed by a line of intermittently, longitudinally spaced voids 25, and the voids of adjacent strips are circumferentially aligned. However, the strip 23 could alternatively be formed by voids in the form of a continuous groove, channel, or other removal of material in a longitudinal configuration from the wall of the inner member 16 which similarly reduces the flexural modulus therealong.

Figure 2:
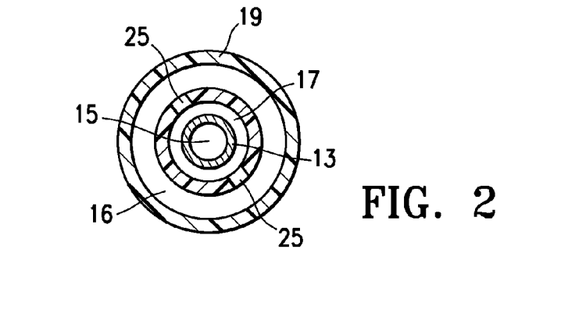
FIG. 2 is a transverse cross section of the catheter of FIG. 1, taken along line 2-2.
Figure 3:
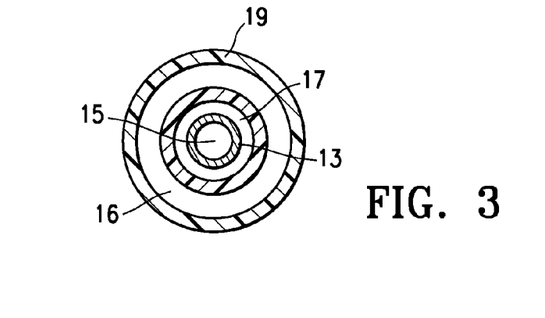
FIG. 3 is a transverse cross section of the catheter of FIG. 1, taken along line 3-3.

The voids 25 are defined by spaced apart edges of sidewall, exposed in the space created by eliminated wall material (i.e., the normal wall thickness around the circumference of the shaft is absent or reduced at the voids by mechanically removing part of the formed tubular shaft wall, or otherwise forming the tubular wall with missing material to form the voids 25), unlike a slit merely cut through the wall of the shaft. In the embodiment of FIG. 1, the voids 25 are holes extending fully through the wall of the inner tubular member 16 from the outer surface into the lumen of the inner member 16, as best shown in FIG. 2 illustrating a transverse cross section of the catheter of FIG. 1, taken along line 2-2. Forming the holes extending fully through the shaft wall provides for ease of manufacture. Additionally, because the voids 25 are always covered by the sheath member 19, any rough edges formed by cutting the holes through the shaft wall are prevented from damaging the patient's anatomy. Alternatively, the voids 25 could be partial voids extending only partially through the wall of the inner tubular member 16. Voids extending only partially through the wall of the shaft avoid disadvantageously weakening the shaft along the shaft section. Additionally, partial voids are preferred in embodiments in which voids extending fully through the shaft wall would disadvantageously prevent shaft lumen integrity, as in the case of voids placed in a wall of a tubular member having an inflation lumen therein.

Figure 4:
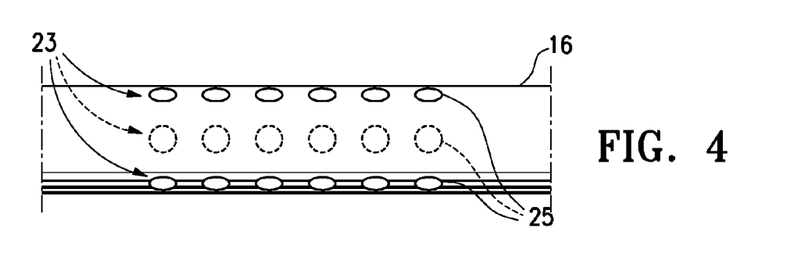
FIG. 4 illustrates an elevational view of an alternative embodiment, in which the incremental rotation inducing features are three strips spaced apart in 120 degree increments.

In the embodiment of FIG. 1, the strips 23 are 180 degrees apart. The incremental rotation inducing section thus consists of two strips 23 of lower flexural modulus equally spaced circumferentially apart on opposite sides of the shaft by two higher flexural modulus solid walled portions of the shaft wall. The strip 23 on the back side of the shaft is illustrated in dashed line in FIG. 1. Although it is not necessary to equally space the strips 23, it is preferred in order to create equal rotational increments that equalize the forces that tend to retain a rotational orientation increment at or near the desired change in rotational orientation and the forces required to overcome rotational orientations between the increments. This provides for ease of use by providing a uniform amount of rotation the user must apply to effect each incremental change in rotational orientation. When confined in a curved conduit, this portion of the shaft will tend to whip to orientations where one of the lower modulus strips 23 of voids 25 aligns with the inside of the curve, such that it has two rotational increments. FIG. 4 illustrates an alternative embodiment similar to the embodiment of FIG. 1 but having three strips 23 of voids 25 spaced 120 degrees apart (with the strip on the back side of the shaft illustrated in dashed line), which thus has three rotational increments due to the tendency to whip to align a lower modulus strip 23 with the inside of the curve of the confining conduit.

For manufacturability and shaft performance characteristics, the lower flexural modulus strips 23 of a catheter of the invention are preferably provided by voids 25 formed in the shaft wall. However, the different flexural modulus strips in accordance with the invention could alternatively be provided by changing the material composition of the inner tubular member, as for example, by extruding, gluing, melting into position, or otherwise applying or constructing strips of higher or lower flexural modulus on or within the inner tubular member wall. Thus, in alternative embodiments, instead of creating strips 23 of lower flexural modulus by forming voids 25 in the wall of the shaft, the shaft will have materials or components added to (including replacing or displacing wall material of) the shaft wall to create strips of higher or lower flexural modulus than longitudinal portions of the shaft wall circumferentially therebetween. However, the result is the same, in that the shaft will tend to whip to orientations where one of the lower modulus longitudinal shaft portions aligns with the inside of the curve. In many embodiments, it is preferably to replace shaft wall material in order to prevent or minimize any increase in the shaft outer diameter or decrease in the inner diameter of the shaft lumen or, if the strips 23 are exposed to the anatomy, to prevent the edges or uneven surfaces at the strips 23 from damaging the anatomy. In addition to forming the strips 23 by providing voids or a different material than the surrounding portion of the wall of the shaft, the strips 23 of a different flexural modulus can alternatively be formed by treating the shaft material to change its material properties along the desired location of the strips 23, thereby forming an integral, one-piece solid walled shaft section which nonetheless has the incremental rotation inducing features 12 of the invention. Such material property changes result from heating or cooling temperatures and/or rates locally/differentially applied to the shaft using devices such as lasers, quenching fluids, heat sinks, shielding, and the like.

For example, the tensile yield of 300 series stainless steel tubes designed to be a high value due to the drawing schedule (work hardening) of the tube, and raising the temperature of the wall to the annealing temperature of the stainless steel grade at the desired location of strips 23 can produce orientations that at the "in use" curvature are subjected to strains in excess of their yield values which thus store less energy at that curvature than rotationally adjacent shaft portions that did not reach the annealing temperature. Similarly, superelastic material (e.g., NiTi) shaft may be temperature manipulated to change the modulus characteristics (the stress-strain curve) of the material in a similar manner to produce strips 23 with different loading and unloading stresses, such that the shaft's energy storage changes with rotational orientation at the desired "in use" curvature. It may also be possible to modify the material characteristics of a superelastic material through local modification of the material composition. For example, it may be possible to use laser-induced, vacuum or other deposition techniques to insert an element(s) into the NiTi matrix to change the material composition. For example, by depositing more Nickel locally in a superelastic Nitinol matrix, it may be possible to have untreated portions of the shaft that are superelastic and treated portions that are not super elastic and/or have a changed stress-strain curve, therefore having different energy storage characteristics. In another example, a polymer shaft exhibiting a relatively high modulus/high yield stress in bending, due to the polymeric material being highly longitudinally oriented, can be locally heat treated to reduce or destroy the molecular orientation just along the desired location of strips 23. However, such methods of material property manipulation for providing the incremental rotation inducing features of the invention are less preferred due to manufacturability issues, and are particularly less preferred in small metallic shafts that are solid or have thick walls. Additionally, polymeric shafts may be locally crosslinked to produce strips 23 with different stress-strain curves than circumferentially adjacent portions of the shaft wall that are not crosslinked. Methods that degrade the shaft material properties (stress-strain curve changes) by changing the material's molecular composition using mechanisms such as ultraviolet degradation, oxidation, chemical etching, and the like are not preferred due at least to adverse changes in biocompatibility, particle generation, shelf-life, and the like.

Figure 5:
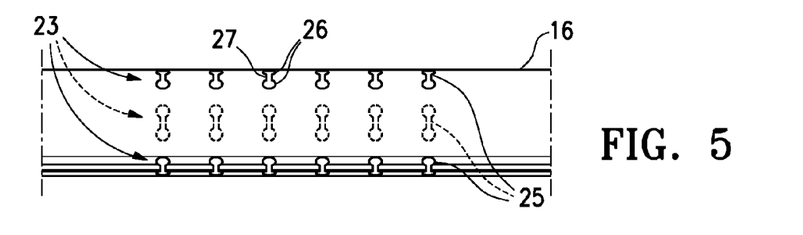
FIG. 5 illustrates an elevational view of an alternative embodiment, in which the incremental rotation inducing features are voids in the shape of dual holes connected by a collapsing slot.

In the embodiment of FIGS. 1 and 4, the voids 25 are substantially circular in shape, and are typically manufactured by drilling or otherwise removing the wall material after formation of the tubular inner member 16. However, the voids 25 could have a variety of suitable shapes including oval, rectangular, or square voids. For example, FIG. 5 illustrates an alternative embodiment in which each void 25 is in the shape of dual holes 26 connected by a collapsing slot 27. As the shaft section having the voids 25 curves in a curved conduit such as the patient's aortic arch, the edges of the slot are brought together which increases the shaft flexural modulus by an amount which preferably prevents or inhibits excessive shaft curvature, while still maintaining a lower stored energy orientation in accordance with the invention. Voids 25 designed to thus interfere with each other at a specific curvature to help limit the curvature of the shaft prevent excessive strain in the modified shaft section, thereby minimizing the stress on the shaft at the void location, which may also act as a stress riser, and preventing material failure or buckling. This embodiment may be particularly useful for shafts formed from metals, since metals generally exhibit lower elongation to yield (causing the shaft section to retain a permanent bend and thus, to whip unintentionally) or break than polymers.

During catheter rotation, the operator or the machine performing the rotation may detect the increase in required applied torque as a maximum energy storage orientation is approached and the subsequent decrease in the required applied torque as the maximum storage orientation is passed and the shaft section rotates to or near to the next minimum storage orientation and, thus, be signaled that the next rotational increment has been attained and that if catheter rotation is stopped, it will remain at that rotational increment. Thus, additionally, if the orientation of the anatomical confining conduit (e.g., aortic arch 50 in FIG. 6) relative to the orientation of desired anatomical diagnostic and/or therapeutic site (e.g., sidewall of coronary artery 51 in FIG. 6) is known, then the operative distal end (e.g., shaft needle port 18 in FIG. 6) of the catheter may be oriented on the shaft relative to the orientation of the minimum energy storage feature(s) (e.g., strips of voids 25 in FIG. 6) of the shaft section by design to cause the operative distal end of the catheter to be easily oriented in the direction(s) of the desired anatomical diagnostic and/or therapeutic site(s). It should be understood that, for convenience, discussions of the incremental rotation inducing features that refer to their flexural modulus are referring to the hypothetical flexural modulus of a length of shaft containing the longitudinal feature all around its circumference. As will be apparent to one skilled in the art, the features that are described as causing changes in the flexural modulus of a shaft portion related to the rotational orientation of the shaft portion in the bend (the incremental rotation inducing features) may be described as causing changes in the effective tensile modulus and/or compressive modulus of that longitudinal strip of catheter shaft wall that then results in the desired changes in shaft flexural modulus with changes in the rotational orientation of the bending applied to that shaft section.

Although the illustrated embodiments have two or three lower flexural modulus strips 23, a catheter of the invention can have only one low flexural modulus strip 23 which thus preferentially orients the shaft in a single rotational orientation, or it can have more than two or three strips 23 spaced around the circumference of the shaft. A single low flexural modulus strip 23, is much less preferred than having two or more strips 23, due to the relatively small effect provided by only one low flexural modulus strip 23 being not generally very useful. Typically, relatively small outer diameter shafts for the coronary vasculature will be constructed with no more than three or four strips 23 due to practical considerations. Larger outer diameter shafts are constructed with six or more strips 23 in one embodiment. In theory the shaft could have any number of rotational increments, however, there are practical limitations. For instance, as the number of increments is increased, the difference that can be achieved between the maximum and minimum flexural modulus (difference in stored energy) is decreased. If the difference is so low that it is near or less than the differences due to unintended whipping sources and/or changes in stored energy in other portions of the shaft, then incremental control of the rotation will be lost. All other factors being equal, a catheter with a proximal shaft configuration with a higher torsion modulus can support the incorporation of more rotational increments, without the loss of incremental rotation control, because the shaft loses energy much more rapidly as the incremental rotation feature rotates past a high energy storage orientation and thus, is more likely to not have enough energy to continue to rotate past the next high energy storage orientation, despite unintended variations. A catheter of the invention is thus configured to provide a sufficiently large difference in stored energy (i.e., sufficiently larger than the differences due to unintended whipping sources and/or changes in stored energy in other portions of the shaft) to provide incremental rotation. Also, the lower the difference in maximum and minimum stored energy, the lower the forces tending to keep the shaft at the minimum energy storage rotational orientation. All other conditions being equal, the larger the number of increments, the less accurate and repeatable the increment of rotation. Also, as the number of rotational increments is increased, the change in applied torque during rotation is decreased. At some point, this change in applied torque can no longer be reliably detected by the user or machine applying the rotation. Thus, although incremental rotation may be occurring, it can't be reliably controlled. In one embodiment in which the changes in applied torque can't be readily tactilely detected, the incremental rotation is nonetheless controlled by controlling the amount of rotation applied to the proximal end of the shaft, provided the shaft is in a known conduit curvature and has a known shaft wind-up and rotational incrementation characteristics at that curvature. The amount of rotation in a distal section of such a shaft produced by rotating the proximal end a set amount is therefore calculated rather than being tactilely detectable.

The multiple strips 23 preferably have the same flexural modulus (e.g., the same number and size of voids along each strip 23), as do the solid walled portions of the shaft wall therebetween. In order to rotate in controlled increments by settling into the low stored energy increment during rotation, the shaft must rotate enough to shed an amount of energy sufficient to cause its stored energy to be less than the next energy storage peak. Thus, the shaft is configured such that the maximum energy storage orientations will store substantially equal amounts of energy during rotation, to prevent or inhibit the shaft from having enough stored energy to miss an increment by rotating through one or more of the next maximum energy storage orientations which can otherwise occur if, for example, the next maximum energy storage peak is much lower than the maximum energy storage peak just passed.

The rotational arc of the lower flexural modulus strips 23 (i.e., the width of each strip 23 around a fraction of the shaft's 360 degree circumference) is preferably minimized and/or not greater than the rotational arc occupied by the higher flexural modulus wall portions therebetween. Especially in designs with a relatively small number (e.g., two or three strips 23) of increments, or with larger shaft diameters, this shorter arc of the lower flexural modulus strips 23 tends to increase the energy storage gradients (change in stored energy per unit of rotation) in the vicinity of the lower flexural modulus strips 23, which produces higher forces that tend to keep the shaft's rotational orientation within tighter rotational limits at each increment (i.e., there is less rotational variability or "play" in orientation of the shaft when the shaft settles into one of the low stored energy gradient valleys). Specifically, as the shaft rotates past an energy storage maximum orientation, its rotation rate speeds up and it releases energy, and when it rotates into the region of the adjacent energy storage minimum, it will pass this minimum to the extent that its actual stored energy is above the minimum energy of this orientation. Put another way, the shaft will keep rotating up the energy storage gradient approaching the next energy storage maximum until the shaft's actual stored energy equals the energy on that gradient. Thus the narrower that gradient, the more confined in rotational orientation will be the final stopping rotational orientation of strip 23 when the operator stops applying rotation to the proximal end of the shaft. These higher gradients also produce more rapid changes in the applied torque, which increases the ease with which they are tactilely detected by the user or a machine and thus, the user or machine may more easily be cued stop rotation of the proximal end of the shaft and keep strips 23 at the desired/designed rotational orientation increment.

The catheter energy storage gradients are defined based on the changes of energy storage in the shaft between where a discrete shaft rotation is applied and the location of the strips 23 at the curved conduit's bend (radius and arc) in different strips 23 rotational orientations and thus, they represent static shaft (no rotation) energy storage. In the dynamic case (with an applied proximal shaft rotation), the rotation of the catheter shaft at the strips 23 in the confining curved conduit depends on the actual current stored energy in the shaft between where the shaft rotation is applied and the location of the strips 23. In general, if the actual current stored energy of the shaft is different than the stored energy value of the gradient, the location on the shaft of the strips 23 will be unstable (rotating/tending to rotate). If the gradient is toward increased shaft energy storage, the rotation of strips 23 will be slowing down and will stop rotating if the actual energy stored in the shaft is equal to the energy on the gradient. The more rapid the increasing stored energy gradient, the fewer degrees strips 23 must rotate to reach equality between any given actual shaft energy storage condition and gradient energy. If the actual stored energy is greater than the maximum stored energy of the gradient, the strips 23 will rotate through that maximum. If the gradient is toward decreased shaft energy storage, the rotation rate change will depend on how fast the shaft is losing energy. If the shaft is losing energy faster than the decreasing gradient, strips 23 rotation rate will slow and it will stop rotating at a point where the actual stored energy equals the gradient energy. In the case of strips 23 stopping rotation, the more rapid the decreasing gradient, the closer in rotational orientation to the gradient minimum will strips 23 stop rotating. If the shaft is losing energy slower than the decreasing gradient, strips 23 rotation rate will increase and strips 23 will rotate past the gradient's minimum. All other properties being equal, the amount of energy released (lost) by the shaft is directly related to both the (square of the) angle that strips 23 rotates through relative to where the user applies rotation and the shaft's torsion modulus between where the shaft rotation is applied (the proximal end of the catheter) and the location of the strips 23 minus the energy applied by the operator to continue rotating the proximal end of the catheter. Thus, with fewer strips 23, there are more rotational degrees of arc between gradient maximums and minimums and more energy will be lost by the shaft as it rotates toward a gradient minimum and so, shafts with fewer strips 23 are more likely to stop rotating strips 23 at or near a gradient minimum. Also, with a larger shaft torsion modulus, the greater the rate of shaft energy loss and so, proximal shafts with greater torsion moduli are more likely to stop rotating strips 23 at or near a gradient minimum. Additionally, if the user rotates the catheter slowly, the energy input to the catheter is minimized and the likelihood of the strips 23 stopping at or near a gradient minimum is increased. Additionally, if the user/machine detects the drop in applied torque, when rotating the catheter and passing a gradient maximum and approaching a gradient minimum, and stops catheter rotation/releases the proximal end of the catheter, the actual stored energy of the catheter shaft will drop to a low level and strips 23 will tend to rotate closer toward the rotational orientation of the gradient minimum, regardless of whether the rotational position is on an increasing or decreasing portion of the gradient.

The longer the longitudinal length of the section within the curved conduit, the greater the possible change in shaft energy storage during rotation and thus the more detectable and controlled the increments will be for the user. However, the catheter is preferably configured such that the features 12 remain confined within the intended curved conduit during the diagnostic or therapeutic treatment (taking into account the length of the intended curved conduit and the longitudinally advanced or withdrawn positions of the catheter during use), and do not become positioned within a different curved conduit which would cause undesired changes in orientation or applied torque during use of the catheter. For example, in one embodiment in which the features 12 are configured to reside in the patient's aortic arch when the distal end of a 3 French catheter (1 mm) is positioned in a portion of the left coronary artery distal to the left main in an adult, the length of the section having features 12 is about 5 mm to about 30 mm, and the distal end of the section having features 12 is about 13 cm to about 30 cm from the distal end of the catheter 10.

Additionally, the length of the section having features 12 is preferably configured such that the maximum twist of the section over its length is substantially less than the designed rotational increments. As the twist of the section approaches the designed rotational increment, the change is stored shaft energy with rotation approaches a minimum and its ability to cause incremental whipping is reduced or eliminated. Thus, the catheter of the invention is unlike prior shaft designs which attempted to minimize whipping by intentionally inducing twisting in or spiraling of the shaft or shaft elements that would otherwise be responsible for inducing whipping.

The incremental rotation inducing features 12 are thus provided along a relatively short section of the elongated catheter shaft, which is known to be confined in a curved conduit during use of the catheter, in such a manner that the section is forced by the conduit to assume a curved shape when the distal end of the catheter is in a desired location within the patient's anatomy. In a presently preferred embodiment of needle catheter 10, the section is configured to reside in the patient's aortic arch during a medical procedure in which the distal end of the catheter 10 is positioned in the patient's coronary artery or heart chamber.

Figure 6:
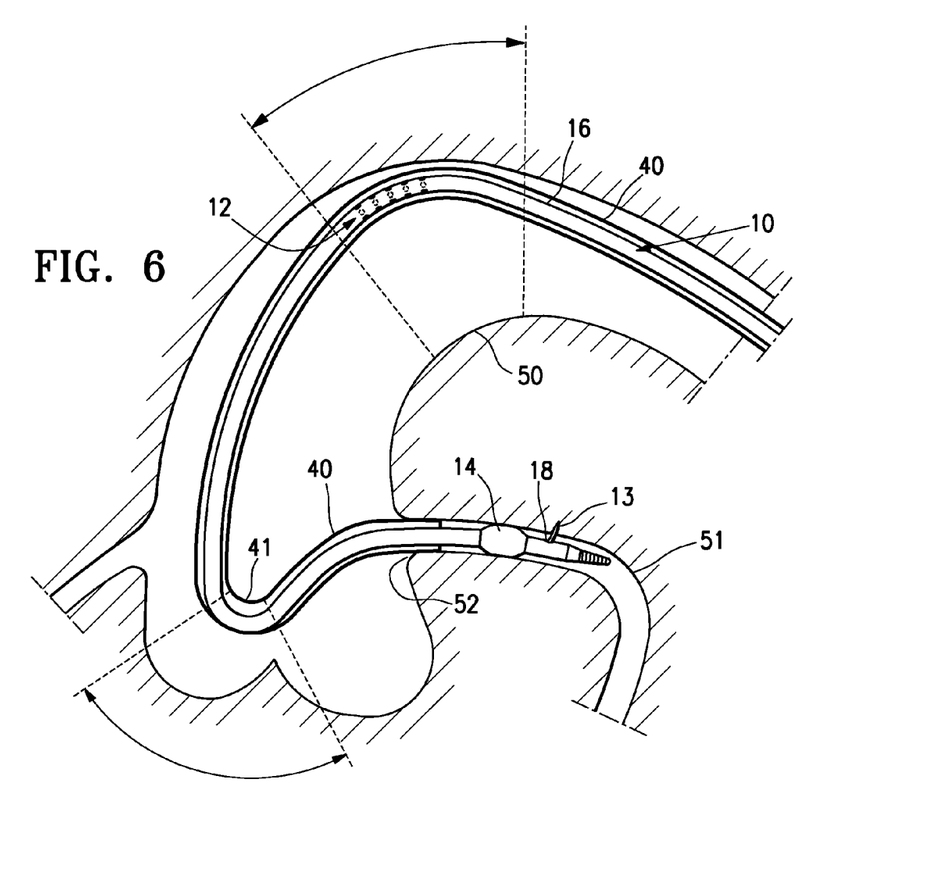
FIG. 6 illustrates the needle catheter of FIG. 1 in the patient's coronary vasculature during a medical procedure, with the incremental rotation inducing features confined in the curved conduit of the patient's aortic arch.

FIG. 6 illustrates a needle catheter 10 with the section having voids 25 residing in the curved conduit of the aortic arch 50 and the shaft needle port 18 positioned in a coronary artery 51. The catheter 10 is in a guide catheter 40, and for ease of illustration the guide catheter 40 is shown in longitudinal cross section and the outer deployment sheath 19 is omitted from FIG. 6. The length of a distal section of the shaft, extending from the distal end of the section having features 12 to the needle port 18, is preferably designed to minimize whipping and has a sufficiently high torsion modulus and low flexural modulus in the shaft portions distal to the features 12, such that the needle port 18 distally spaced from the section having features 12 will rotate by following the incremental rotation of the section having features 12. Thus, the distal section (distal to the section with features 12) preferably has a high torsion modulus to flexural modulus ratio, and a very uniform flexural modulus or curved moment, to minimize whipping therealong to at least a degree such that the incremental rotation operation of features 12 are not substantially interfered with and port 18 substantially follows the rotational orientation changes of features 12.

As illustrated in FIG. 6, other curved conduits exist that could alternatively be exploited for inducing the incremental rotation in accordance with the invention, such as a preformed curve in the distal section of the guide catheter 40, or a curve of the coronary artery 51 itself. Although the features 12 are ideally located in the shaft as close as possible to the operative distal end component to be oriented (e.g., the shaft needle port 18) in order to minimize wind-up and whipping occurring at the operative distal end component, making use of the curves of the coronary artery and guide catheter 40 are not presently preferred. Specifically, the curves of the coronary artery, especially at the proximal locations contemplated for needle injections (e.g., no more than about 10 cm into the vessel), are highly variable such that incremental control of rotation is not reliable and therefore, not preferred. The ostial engagement curve 41 of a guide catheter, proximal of the ostium 52, is reliable by design and typically not more than about 3 to 5 cm long depending on the size of the patient and the choice of guide catheter type, whereas the typical injection sites are likely to be separated by a distance of more than 3 cm (e.g., injections along a length of up to about 6 to about 8 cm of the coronary artery 51). This problem can be mitigated by providing the section with the features 12 over a relatively long length of the shaft, longer than 3 cm (e.g., 6 to 15 cm), to ensure that at least a minimum length of feature 12 is in the curve 41 of the guide catheter 40 at any treatment/diagnostic position in the coronary artery. Although the more distal of these features 12 may become positioned in a curved portion of the coronary artery or aortic arch and thus interfere with the incremental rotational orientation of the needle exit port 18, the system is preferably configured such that the incremental rotation along the section with features 12 nonetheless translates to the distal end of the catheter. Specifically, configuring the catheter to have the section with features 12 reside in the ostial engagement curve 41 of the guide catheter 40 is preferably limited to embodiments in which the curvature of guide catheter curve 41 is greater (has a smaller radium of curvature) relative to the curvature of the vessel to be treated and/or the curvature of the aortic arch, such that the effects produced by the curvature of curve 41 are dominant and not substantially interfered with by the effects of a portion of features 12 being curved in the aortic arch or a vessel. Although the described embodiment locates the features 12 proximal of the operative feature of the catheter (e.g., needle port 18), it is contemplated in other applications, where a conveniently positioned curved conduit is distal to the region to be treated and/or diagnosed, that the operative feature(s) of the catheter or device may be located proximal of the features 12. Thus, although the operative distal portion of the shaft (e.g., shaft needle port 18) is typically distal to the confining curved conduit, in some embodiments it is proximal to the curve.

In one embodiment, the catheter has the features 12 in both the section of the shaft residing in the aortic arch 50 and the more distal section that resides in the curve 41 of the guide catheter 40, provided the features will be longitudinally aligned and curving in the same direction in the two curved conduits, to thereby work together to orient the distal end of the catheter. However, because it can be difficult to ensure this, in a presently preferred embodiment, the section of the shaft having features 12 is sufficiently short so that the features are in only one of the curved conduits (e.g., just the aortic arch and not the ostial engagement curve of the guide catheter).

In embodiments in which the orientation of the curved conduit (e.g., the aortic arch) relative to the anatomy to be treated/diagnosed is known or is within suitable limits, the lower flexural modulus strips 23 are preferably longitudinally aligned with the operative distal end component (e.g., the shaft needle port 18), to facilitate rotationally orienting the shaft in such a way as to ensure that the component is directed toward the desired treatment/diagnosis site or away from a non-desired site in the anatomy at, at least, one rotational increment.

The catheter 10 is thus configured to facilitate orienting an operative distal portion of a catheter in a patient's body lumen for performing a medical procedure. For example, as illustrated in FIG. 6, needle catheter 10 is introduced into the patient's vasculature, typically within a previously positioned guide catheter 40, and advanced therein until the needle port 18 of the catheter 10 is distal to the distal end of the guide 40 and advanced to a desired injection site. The catheter is configured such that the incremental rotation inducing shaft section having features 12 is in a curved configuration caused by being in the curve of the aortic arch 50. The shaft needle port 18 is then oriented in the desired rotational orientation artery 51, typically while being viewed therein under fluoroscopy, so that the needle 13 will emerge from the port 18 and into the artery wall at the desired location. Specifically, to orient the port 18, the method includes inducing controlled whipping in rotational increments by rotating the proximal end of the shaft by an amount which thereby rotates the distal end of the shaft in a rotational increment defined by the circumferential spacing between the strips as the shaft twists through one of the high stored energy orientations to one of the low stored energy orientations, one or more times until the port 18 is suitably rotationally oriented in the artery. The needle is then extended out the port 18 to perform a medical procedure, such as injecting agent from the needle into the periadventitial space from where it infuses to the target plaque. Preferably, the user or machine rotating the proximal end of the shaft can tactilely feel the rotational increments, and uniform rotation is applied to effect each incremental rotation, as discussed above. After an initial injection, the needle can be retracted into the shaft and the port repositioned in the artery for additionally injections. Experiments indicate that injections made into the periadventitial space of a coronary artery distribute around the artery over a total arc of about 180°. Thus, to treat the entire diameter of the artery will require two or possibly three roughly equal rotationally spaced injections. Thus, the catheter 10 facilitates thoroughly and accurately treating a desired region in the artery, by controllably displacing the port both longitudinally and rotationally in the artery.

In a catheter of the invention, the shaft having the incremental rotation features 12 in a section thereof can be formed of a variety of suitable materials and designs including polymeric, metallic, and composite tubular members commonly used in catheter shaft construction. For example, in one embodiment, the inner member 16 is formed of a metallic tubular member at least along the section having features 12 and typically along the sections proximal and distal thereto. The inner member 16 having the needle 13 slidably disposed therein is typically a high strength member formed of metal or a high strength polymer such as polyimide. The shaft can be formed multiple sections/tubular members joined end to end providing a changing shaft composition, or have a uniform composition along all or part of its length include the shaft section having features 12 and sections proximal and distal thereto.

In one embodiment, the composition of the elongated tubular shaft changes at the section having the features 12, such that the shaft has an average flexural modulus substantially equal to an average flexural modulus of longitudinally adjacent portions of the shaft along which the feature strips 23 do not extend. For example, in the embodiment in which the strips are voids or otherwise provide a lower flexural modulus along the strips, the tubular member along the section with the voids is purposely formed of a different material or design with a higher flexural modulus than sections of the tubular member immediately proximally and distally adjacent thereto, to even out the overall flexural modulus of the shaft. Similarly, in embodiments in which the strips consist of a stiffer material than material forming the circumferentially adjacent shaft wall portions between adjacent strips, the tubular member along the section with the stiffer strips is formed of material with a lower flexural modulus than sections of the tubular member immediately proximally and distally adjacent thereto to even out the overall flexural modulus of the shaft. As a result, the section having the strips 23 can be positioned in the curved section with less likelihood of kinking or damaging the shaft along the incremental rotation inducing section, despite the change of the overall flexural modulus caused by the voids 25. If the overall flexural modulus of the section of the shaft with the voids 25 is significantly smaller than the proximally or distally adjacent sections, then the curvature of the adjacent sections will tend to be shifted this lower flexural modulus section, potentially causing damaging strains or unacceptably weakening the section by unacceptably lowering its resistance to kinking, torsion modulus/failure torque, or compression or tensile failure force. Many factors influence kinking, like the curve of the confining conduit, the shaft cross-sectional dimensions, and the influence of the guide catheter's and deployment sheath's flexural modulus. However, in general, all other factors being equal, the greater the difference in flexural modulus between an incremental rotation inducing feature section's flexural modulus at a particular rotational orientation, the less curvature is required to cause a bending kink failure. Sure failures may occur within section 12, or just proximal or distal thereto, wherever the flexural modulus is lowest. Additionally or alternatively, kinking may be due to a torsional (torque) failure. Thus, section 12 is preferably designed such that it does not fail at torques less than the torque required to rotate the distal end of the catheter in the anatomy. In general, the embodiment of the invention which maintains the average (averaged rotationally) shaft flexural modulus in the design of section 12 near that of the adjacent shaft sections, also tends to increase the section 12 torque failure value. Plus, in addition to avoiding a very weakened shaft section, the difference between the maximum and minimum stored energy rotational orientations can be maintained or even increased in the embodiment in which the tubular member along the section with strips 23 is formed of a different material than the immediately proximally and distally adjacent sections.

Although the incremental rotation inducing features are in the inner tubular member 16 in the embodiment of FIG. 1, they could be provided in alternative parts of the shaft which are rotationally constrained relative to the operative distal end component (e.g., shaft port 18) to be oriented. For example, in embodiments in which the deployment sheath 19 is so constrained relative to the inner member 16 at locations thereaolong which are not limited to just the proximal end at the adapter 20 (for example at or near the section that resided in the aortic arch during use, or anywhere distal thereto), then the features 12 are preferably provided in the wall of the deployment sheath 19 rather than the inner member 16. The deployment sheath 19 has a large outer diameter than the inner member 16 and is typically formed of a polymeric tubular member which facilitates forming the features 12 in the wall of the deployment sheath 19, as compared to the inner member 16 which is normally metallic.

The dimensions of catheter 10 depend upon factors such as the catheter type and the size of the artery or other body lumen through which the catheter must pass. By way of example, in a coronary embodiment, the shaft 11 inner tubular member 16 typically has an outer diameter of about 0.015 to about 0.016 inch (0.38 to 0.41 mm) and a wall thickness of about 0.002 to about 0.004 inch (0.05 to 0.10 mm), and the deployment sheath member 19 typically has an outer diameter of about 0.040 to about 0.045 inch (1.0 to 1.14 mm) and a wall thickness of about 0.006 to about 0.012 inch (0.15 to 0.30 mm). The overall length of the catheter 10 may range from about 100 to about 150 cm, and is typically about 143 cm.

A variety of suitable agents can be delivered using a catheter and method of the invention. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. Suitable therapeutic agents include, but are not limited to, thrombolytic drugs, anti-inflammatory drugs, anti-proliferative drugs, drugs restoring and/or preserving endothelial function, and the like. A variety of bioactive agents can be used including but not limited to peptides, proteins, oligonucleotides, cells, and the like. The agent is typically a therapeutic agent for restenosis, although the agent can be delivered for a variety of treatment procedures, including treatment of a diseased (occluded) blood vessel by delivery of the agent directly to the diseased blood vessel, or treatment of the myocardium of the heart by delivery of an agent to one of the (healthy) coronary arteries. In a presently preferred embodiment, the agent is an anti-inflammatory agent including steroids, or is an agent that induces cholesterol efflux from arterial wall plaque including ApoAI mimetic peptides, PPARα agonists. In addition to therapeutic agents, a variety of diagnostic agents can be used according to the present invention. The agent may be provided in a variety of suitable formulations and carriers including liposomes, polymerosomes, nanoparticles, microparticles, lipid/polymer micelles, and complexes of agents with lipid and/or polymers, and the like.

Although discussed primarily in terms of an embodiment in which the incremental rotation inducing features 12 are provided in a needle catheter having a needle which extends through a needle exit port in a side wall of the shaft, it should be understood that a catheter of the invention can be configured for different uses and with a variety of suitable alternative designs. Although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

I claim:

1. A method of orienting an operative distal portion of a catheter in a patient's body lumen for performing a medical procedure, comprising
   a. advancing a catheter within a patient's body lumen to position the operative distal portion at a desired region in the patient's anatomy, the catheter having a tubular shaft comprising a proximal end, a distal end, and a tubular member having an incremental rotation inducing section along which a wall of the shaft has one or more strips circumferentially surrounded by portions of the wall having a different flexural modulus than the strips, such that longitudinal shaft portions are separated circumferentially by a longitudinal shaft portion of a higher or lower flexural modulus configured to provide the shaft in a curved configuration with one or more relatively low stored energy orientations and one or more higher stored energy orientations; and
   b. inducing controlled whipping in rotational increments by positioning the incremental rotation inducing section of the shaft in a curved section of a delivery catheter, in which the shaft section is in the curved configuration, and then rotating the proximal end of the shaft by an amount which thereby rotates a more distal location of the shaft in a rotational increment as the shaft twists through one of the high stored energy orientations to one of the low stored energy orientations, one or more times, to orient the operative distal portion of the catheter at a desired rotational orientation in the patient.

2. The method of claim 1 wherein the shaft has two or more strips circumferentially spaced apart by portions of the wall having a higher flexural modulus than the strips, such that the shaft has two or more relatively low stored energy orientations and two or more higher stored energy orientations and inducing the controlled whipping in b) comprises rotating the shaft in the rotational increment defined by the circumferential spacing between the strips.

3. The method of claim 2 wherein the strips are uniformly spaced apart around the circumference of the tubular member such that uniform torque is applied in b) to effect each incremental rotation.

4. The method of claim 3 wherein the higher stored energy orientations have substantially equal maximum stored energy values, such that energy stored in the shaft by the rotation of the proximal end is fully shed as the distal end rotates through the higher stored energy orientation, so that the resulting distal rotation stops when the shaft reaches the adjacent low stored energy orientation.

5. The method of claim 2 wherein the incremental rotation inducing section of the shaft has an average flexural modulus substantially equal to an average flexural modulus of longitudinally adjacent portions of the shaft along which the strips do not extend, and b) comprises positioning the strips in the curved section without kinking or damaging the shaft along the incremental rotation inducing section.

6. The method of claim 1, further comprising:
injecting fluid from the operative distal portion of the catheter into the patient's tissue at a first location on the tissue; and
injecting fluid from the operative distal portion of the catheter into the patient's tissue at a second location of the tissue, the second location spaced apart from the first location by an incremental rotation of the operative distal portion resulting from the induced controlled whipping.

7. The method of claim 1, wherein the one or more strips each includes a plurality of holes extending from a longitudinal lumen of the shaft and fully through the wall of the shaft.

8. The method of claim 7, wherein, in each of the one or more strips, the holes are intermittently spaced longitudinally.

9. The method of claim 7, wherein each of the holes contain material having a higher flexural modulus than longitudinal shaft portions surrounding the one or more strips.

10. The method of claim 1, wherein the operative distal portion of the catheter includes a hollow needle.

11. The method of claim 10, further comprising injecting fluid from the hollow needle into the patient's tissue at a plurality of locations on the tissue, the plurality of locations spaced apart from each other by incremental rotations resulting from the induced controlled whipping.

12. The method of claim 10, wherein the needle is disposed within a longitudinal lumen of the shaft, a plurality of holes extending from the lumen to an outer surface of the shaft.

13. The method of claim 12, wherein the catheter further comprises a sheath configured to be slidably retracted from shaft to deploy the needle.

14. A method of orienting an operative distal portion of a catheter in a patient's body lumen for performing a medical procedure, the method comprising:
advancing a catheter within a patient's body lumen, the catheter having a shaft comprising an incremental rotation inducing section along which a tubular wall of the shaft has one or more longitudinal strips circumferentially surrounded by portions of the wall having a different flexural modulus than the strips to provide the shaft with one or more relatively low stored energy orientations and one or more higher stored energy orientations; and
inducing controlled whipping in rotational increments by positioning the incremental rotation inducing section of the shaft in a curved configuration, and then rotating a proximal end of the shaft by an amount which rotates an operative distal portion of the catheter in a rotational increment as the shaft twists through one of the high stored energy orientations to one of the low stored energy orientations, one or more times, to orient the operative distal portion at a desired rotational orientation relative to tissue of the patient,
wherein the incremental rotation inducing section has an average flexural modulus substantially equal to an average flexural modulus of longitudinally adjacent portions of the shaft along which the strips do not extend.

15. The method of claim 14, wherein the one or more strips each includes a plurality of holes that are longitudinally aligned and extend from a longitudinal lumen of the shaft and fully through the wall of the shaft.

16. The method of claim 14, wherein catheter further includes a needle and a sheath covering the shaft, the needle disposed within a lumen of the shaft, a plurality of holes extending from the lumen to an outer surface of the shaft, the sheath configured to be slidably retracted from the shaft to allow deployment of the needle.

17. The method of claim 14, further comprising injecting fluid from the operative distal portion of the catheter into the patient's tissue at a plurality of locations on the tissue, the plurality of locations spaced apart from each other by incremental rotations during the controlled whipping.

18. A method of orienting an operative distal portion of a catheter in a patient's body lumen for performing a medical procedure, the method comprising:
advancing a catheter within a patient's body lumen, the catheter having a shaft comprising an incremental rotation inducing section along which a tubular wall of the shaft has one or more longitudinal strips circumferentially surrounded by portions of the wall having a different flexural modulus than the strips to provide the shaft with one or more relatively low stored energy orientations and one or more higher stored energy orientations; and
inducing controlled whipping in rotational increments by positioning the incremental rotation inducing section of the shaft in a curved configuration, and then rotating a proximal end of the shaft by an amount which rotates an operative distal portion of the catheter in a rotational increment as the shaft twists through one of the high stored energy orientations to one of the low stored energy orientations, one or more times, to orient the operative distal portion at a desired rotational orientation relative to tissue of the patient,
wherein the one or more strips each includes a plurality of holes that are longitudinally aligned and extend from a longitudinal lumen of the shaft and fully through the wall of the shaft.

19. The method of claim 18, wherein catheter further includes a needle and a sheath covering the shaft, the needle disposed within the lumen of the shaft, the plurality of holes extending from the lumen to an outer surface of the shaft, the sheath configured to be slidably retracted from shaft to allow deployment of the needle.

20. The method of claim 18, further comprising injecting fluid from the operative distal portion of the catheter into the patient's tissue at a plurality of locations on the tissue, the plurality of locations spaced apart from each other by incremental rotations during the controlled whipping.

21. The method of claim 1, wherein the curved section of the delivery catheter is located within the patient's aortic arch and a distal end of the incremental rotation inducing section is about 13 cm to about 30 cm from the distal end of the shaft.

22. The method of claim 1, wherein the curved section of the delivery catheter is an ostial engagement curve proximal to the patient's ostium.

* * * * *